(12) United States Patent
Marchetti

(10) Patent No.: US 8,430,829 B1
(45) Date of Patent: Apr. 30, 2013

(54) ARTICLE FOR USE WITH ORTHOPEDIC IMMOBILIZATION APPARATUS

(76) Inventor: Kelly A. Marchetti, Natick, MA (US)

( * ) Notice: Subject to any disclaimer, the term of this patent is extended or adjusted under 35 U.S.C. 154(b) by 219 days.

(21) Appl. No.: 12/725,996

(22) Filed: Mar. 17, 2010

(51) Int. Cl.
*A61F 5/00* (2006.01)

(52) U.S. Cl.
USPC .................................. 602/3; 602/60; 602/65

(58) Field of Classification Search ............... 602/3–5, 602/8, 20–27, 60–65; 128/845, 846, 848, 128/856
See application file for complete search history.

(56) References Cited

U.S. PATENT DOCUMENTS

| | | | | |
|---|---|---|---|---|
| 2,956,561 A * | 10/1960 | Houde | | 602/3 |
| 4,646,727 A * | 3/1987 | Chambers | | 602/3 |
| 5,735,807 A | 4/1998 | Cropper | | |
| 6,579,252 B2 * | 6/2003 | Lloyd et al. | | 602/60 |
| 6,916,301 B1 * | 7/2005 | Clare | | 602/3 |
| 7,066,899 B2 | 6/2006 | Baron | | |
| D583,478 S | 12/2008 | Hargrave et al. | | |
| 7,475,501 B1 | 1/2009 | DeToro et al. | | |
| 7,887,495 B2 * | 2/2011 | Boyd et al. | | 602/3 |
| 2003/0191419 A1 * | 10/2003 | Melin et al. | | 602/3 |
| 2006/0084896 A1 | 4/2006 | Baron | | |
| 2006/0224094 A1 | 10/2006 | Baron | | |
| 2010/0256542 A1 * | 10/2010 | Nausid | | 602/3 |
| 2011/0088284 A1 | 4/2011 | Wruck et al. | | |

* cited by examiner

*Primary Examiner* — Michael A. Brown
(74) *Attorney, Agent, or Firm* — Burns & Levinson LLP; Bruce D. Jobse, Esq.

(57) ABSTRACT

A wearable article, which covers any number of different orthopedic immobilization devices for appendages of either the upper or lower extremities, includes a tubular sleeve of material printed with graphic indicia, including any of a decorative pattern, logo, text, graphic or advertisement, etc. In various disclosed embodiments, the article maybe any of reversible, water repellent, rapidly securable, selectively accessible or capable of storing either a source of scent or other all the object therein.

26 Claims, 14 Drawing Sheets

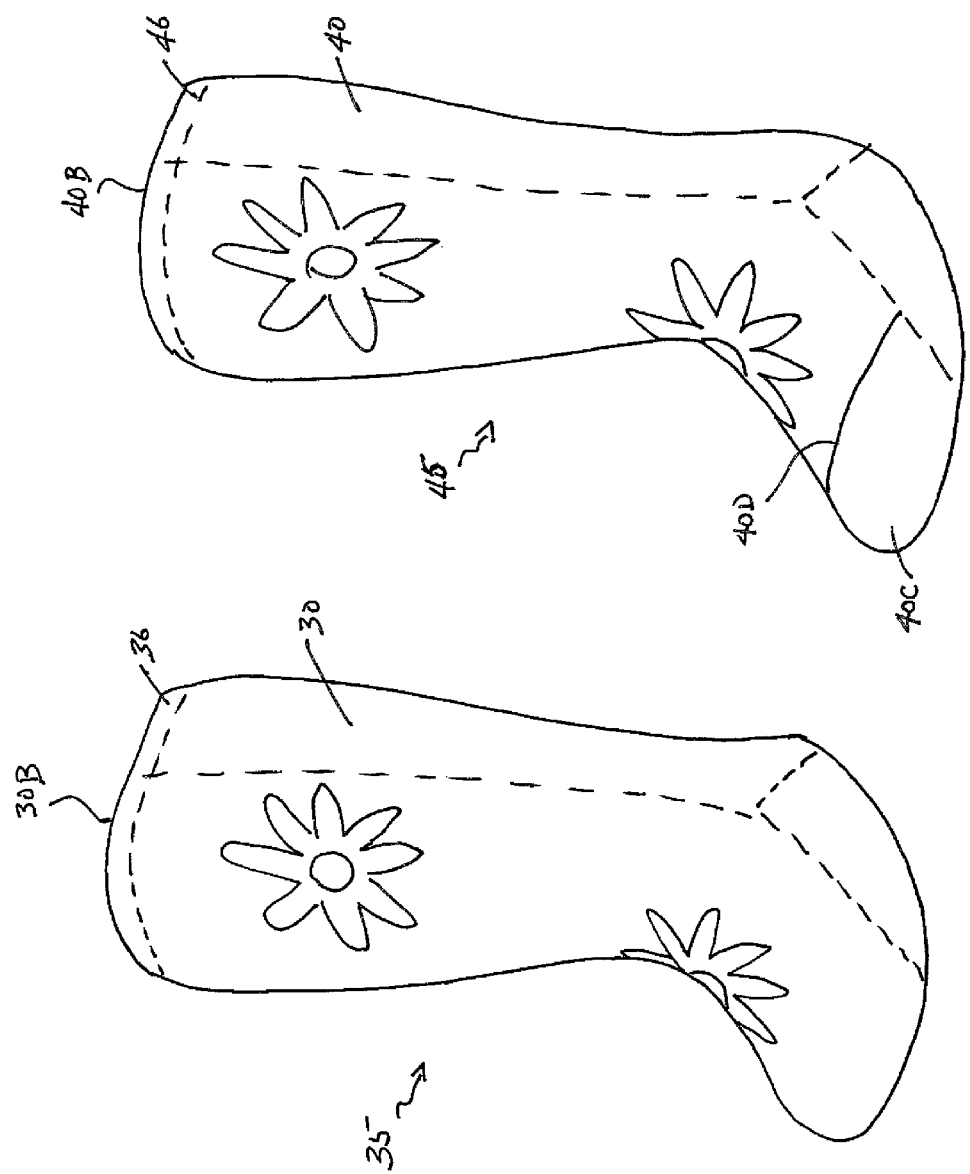

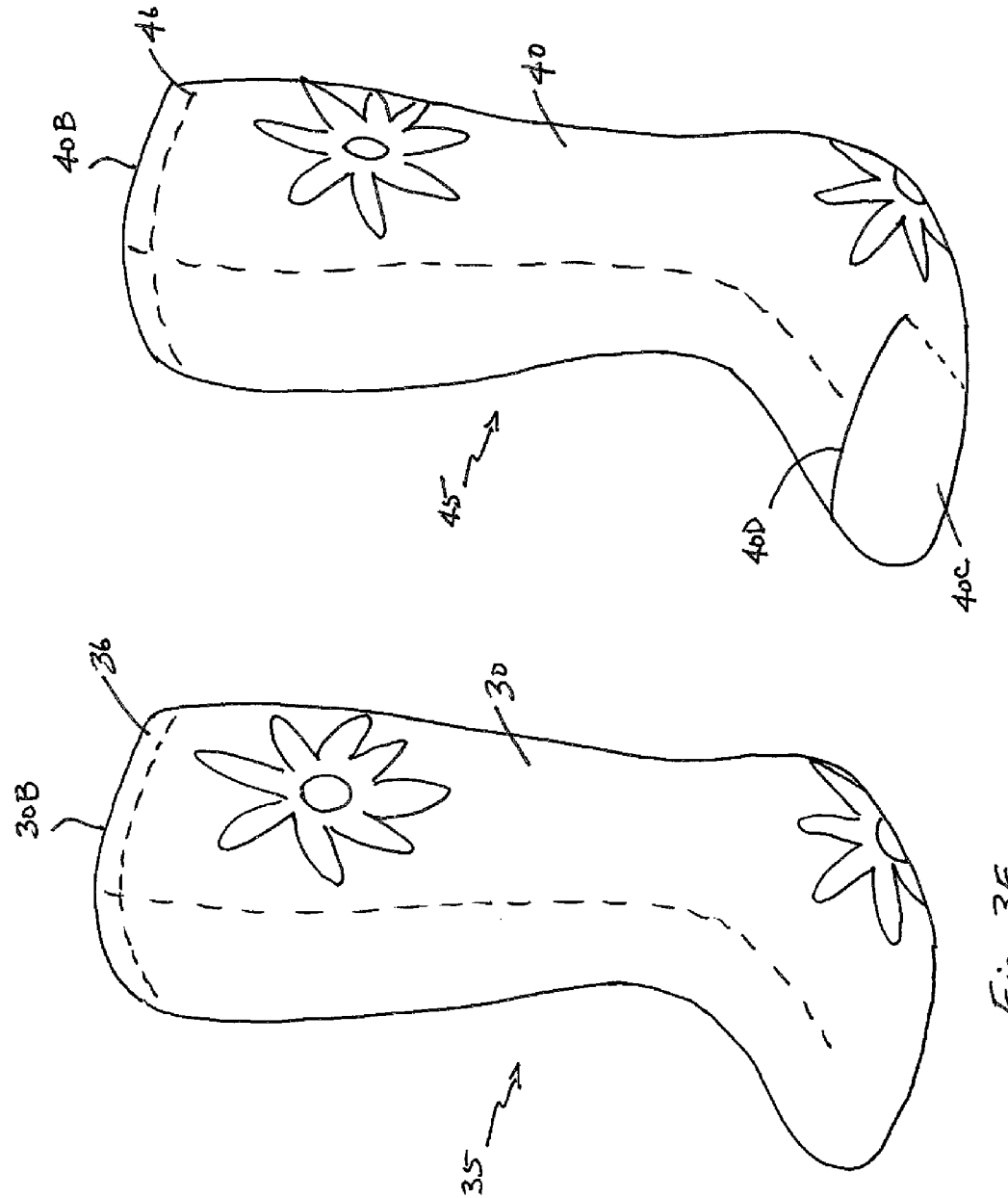

ARTICLE FOR USE WITH ORTHOPEDIC IMMOBILIZATION APPARATUS

FIELD OF THE INVENTION

The disclosed article relates to apparel, and, in particular, to a cover for use with orthopedic immobilization devices.

BACKGROUND OF THE INVENTION

Numerous apparatus or devices are currently used by orthopedic specialists and medical personnel to immobilize injured limbs, including devices such as soft casts, hard casts, walking boots, etc. The primary function of such devices is to immobilize the injury to accelerate the healing process. Such devices must be worn for a period of time which can span from several days to several months, depending on the severity of the injury. Unfortunately, the physical appearance of such devices is often utilitarian and unattractive. The appearance of such devices can have a negative psychological impact on the patient during healing process, particularly if the device must be worn for an extended period of time, further exacerbating any negative feelings towards the injury.

Accordingly, need exists for a cover which may be placed around an orthopedic immobilization device which improves the aesthetic appearance of the device.

A further need exists for a cover which may be placed around an orthopedic immobilization which improves the psychological well-being of the injured party toward the device and/or the injury.

Yet another need exists for a cover which may be placed around an orthopedic immobilization which enables the wearer to express their style or tastes or endorsement of a brand or entity.

In addition, the above problems such immobilization devices, depending on their composition and structure, are usually susceptible to exposure from the elements, most notably rain, snow, etc. This is particularly true for immobilization devices worn on the lower extremities, particularly during seasons with frequent inclement weather.

Accordingly, still a further need exists for a cover which may be placed around an orthopedic immobilization device which protects the underlying device from the elements and which may be easily secured and removed, as necessary.

A further concern associated with long-term use of an orthopedic immobilization device is keeping the device and the immobilized limb fresh smelling.

Accordingly, yet a further need exists for cover which may be placed around an orthopedic immobilization device which contains a pocket or other feature for storing a fragrance source or other item.

SUMMARY OF THE INVENTION

The above-described deficiencies are fulfilled by the article disclosed herein which contemplates a wearable article which covers any number of different orthopedic immobilization devices for appendages of both the upper and lower extremities. The sleeve may be printed with a decorative pattern, logo, graphic, text, advertisement, etc. and, in some embodiments, as will be explained hereinafter, maybe any of reversible, water repellent, rapidly securable, selectively accessible or capable of storing either a source of scent or other object. The disclosed article transforms the bland, institutional look of an orthopedic device into a fashion statement- or a business necessity. Another benefit of the disclosed article is that the cover thereof solves the problem of the hook and loop boot straps, as well as the rougher extremity of the cast, from catching on clothes, blankets or any other materials that are prone to snagging.

According to the first aspect of the disclosure, an article of apparel for covering an orthopedic immobilization device comprises a first sleeve of material defining exterior surface and interior surfaces and extending between first and second ends thereof; a first elastic member secured about one of the first and second ends of the first sleeve; and graphic indicia printed on one of the exterior surface and interior surfaces of the first sleeve. In one embodiment, the first sleeve is substantially tubular, with an L-shaped profile, one of the first sleeve ends defusing an opening larger than the other of the first sleeve ends. In such embodiment, the end with the larger opening is provided with an attachment mechanism which may be implemented with either of the hook and pile portion of an attachment set at multiple locations, with the complementary half of the hook and pile attachment set being securable to the orthopedic immobilization device. In an embodiment useful for covering a foot cast, one end of the sleeve may optionally have a pocket attached thereto and extending outwardly therefrom for use in covering the toes. Such pocket may be secured with an attachment mechanism.

According to a second aspect of the disclosure, one or both ends of the first sleeve have an elastic members secured thereto. In addition, a hole may be present at the one end of the sleeve to allow for insertion of a digit, typically the thumb. In other embodiments, the sleeve may include a pocket for retention of the scent source or other objects.

According to a third aspect of the disclosure, an article of apparel for covering an orthopedic immobilization device comprises first and second sleeves of material defining respective exterior surface and interior surfaces and extending between first and second respective ends thereof; an elastic member may be secured about one of the first and second ends of the first and second sleeves; and graphic indicia printed on one of the exterior surface and interior surfaces of the first and second sleeves. In this embodiment, the second sleeve and first sleeve are concentrically arranged and joined to form a composite sleeve, such that the graphic indicia printed on the first sleeve is positioned on an exterior surface of the composite sleeve in a first configuration and the graphic indicia printed on the second sleeve is positioned on an exterior surface of the composite sleeve in a second configuration.

According to a fourth aspect of the disclosure, an article for covering an orthopedic immobilization device, the article comprises: first and second sleeves of material, each sleeve defining exterior and interior surfaces thereof and extending between first and second ends thereof; first elastic members secured about one of the first and second ends of each of the first and second sleeves; graphic indicia printed on one of the exterior surface and interior surfaces of each of the first and second sleeves; the first and second sleeves being concentrically arranged and joined to form a composite sleeve having a evertable interior and exterior surfaces, wherein the graphic indicia printed on the first sleeve is positioned on an exterior surface of the composite sleeve in a first configuration and the graphic indicia printed on the second sleeve is positioned on an exterior surface of the composite sleeve in a second configuration.

According to a fifth aspect of the disclosure, an article for covering an orthopedic immobilization device comprises: a sleeve of material defining exterior surface and interior surfaces and extending between first and second ends thereof; a first elastic member secured about one of the first and second ends of the sleeve; an aperture extending through the sleeve proximate one of first and second ends thereof and sized to allow a digit to extend therethrough when the article is disposed about an appendage; graphic indicia printed on one of the exterior surface and interior surfaces of the first sleeve; and a pocket attached to the interior surface of the first sleeve.

According to a sixth aspect of the disclosure, an article for covering an orthopedic immobilization device comprises: a sleeve of material defining exterior surface and interior surfaces and having a substantially boot-shaped profile and a first open end and a second end; a first elastic member secured about the first end of the sleeve; graphic indicia printed on the exterior surface of the sleeve; and a pocket attached to the interior surface of the first sleeve.

BRIEF DESCRIPTION OF THE DRAWINGS

The features, objects and advantages of the invention will be better understood by referring to the following detailed description in conjunction with the accompanying drawing in which:

FIGS. 3A-3D illustrate perspective, front, rear, and side views of an article in relation to a foot cast;

FIG. 3E is an alternative embodiment of the article of FIG. 3A;

FIGS. 4A-4D illustrate perspective, front, rear, and side views of an alternative embodiment of the disclosed article of FIGS. 3A-3D;

FIG. 4E is an alternative embodiment of the article of FIG. 4A;

DETAILED DESCRIPTION

Figure 2A:
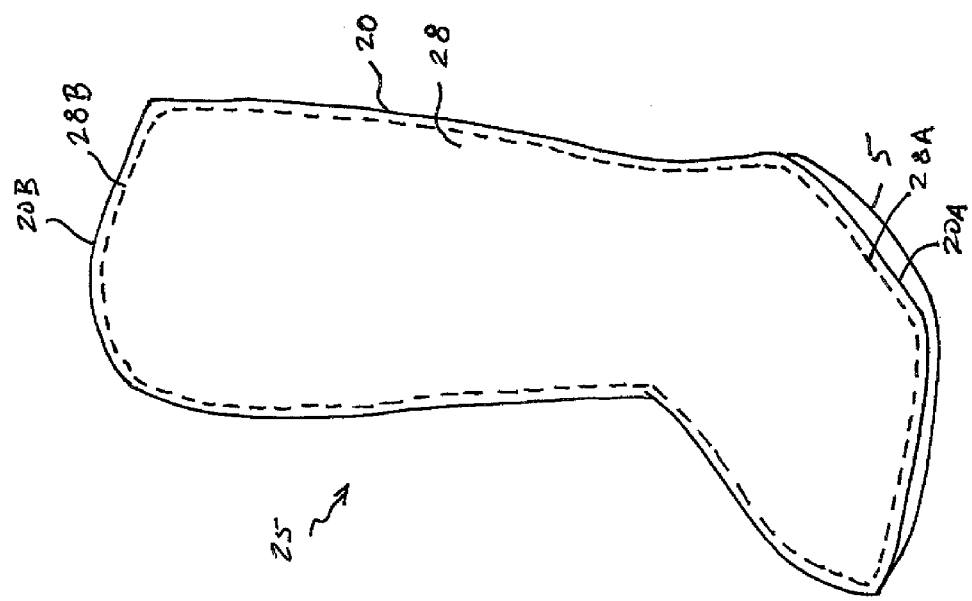
FIGS. 2A-2D illustrate perspective, front, rear, and side views of a reversible article in relation to an orthopedic walking boot.

In FIGS. 1A-6B dashed-lines are used to illustrate exemplary stitching patterns except where noted as specifically illustrating a phantom or invisible portion of an article. Such seems or stitching patterns are exemplary only and are not meant to be limiting as to their location, form, etc.

Referring to FIGS. 1A-D, an article 15 in accordance with the disclosure is illustrated. Article 15 is intended to cover a walking boot orthopedic device such as any of the Equalizer Walker, Equalizer Air Walker, and the Equalizer Pre-Inflated Air Walker all commercially available from Ossur Americas Aliso Viejo, Calif., or the DONJOY walker boots commercially available from DJO, LLC Vista, Calif., or any of the FP, XP or SP walking brace products commercially available from Aircast, Inc. Austin, Tex. In the figures, the sole of the walking boot 5 relative to article 15 is illustrated. In the disclosed embodiment, article 15 comprises a substantially tubular sleeve 10 having a substantially L-shaped profile with a first end 10A having an opening larger than a second end 1013 thereof. Since walking boots are symmetric in design, sleeve 10 is also symmetric in design and can be used on either the right or left foot. One or both ends 10A and 10B may have an elastic band 16 secured about their respective openings to ensure a close fit of sleeve 10 about the walking boot and to prevent sleeve 10 from moving relative to the surface of the walking boot. In FIGS. 1A-D, the location of elastic member 16 is delineated by the stitching near ends 10 A-B, in addition to the corresponding reference numerals.

In one embodiment, sleeve 10 comprises a stretchable fabric that may be breathable, durable and washable to allow air flow through sleeve 10 to keep the immobilized limb or appendage comfortable. Such stretchable fabric may comprise Spandex and/or other combinations of material, including any of LYCRA®, polyester and/or rayon and enables the article 15 to accommodate a range of boot sizes and commercially available configurations. Alternatively, sleeve 10 may be made from a breathable, washable water repellant material, such as rip stop, or other suitable equivalent materials such as a material impregnated with natural or synthetic rubber. Such a water repellent sleeve keeps the boot, foam liner or cast dry during inclement weather to prevent hours of discomfort from dampness or cold.

Figure 1A:
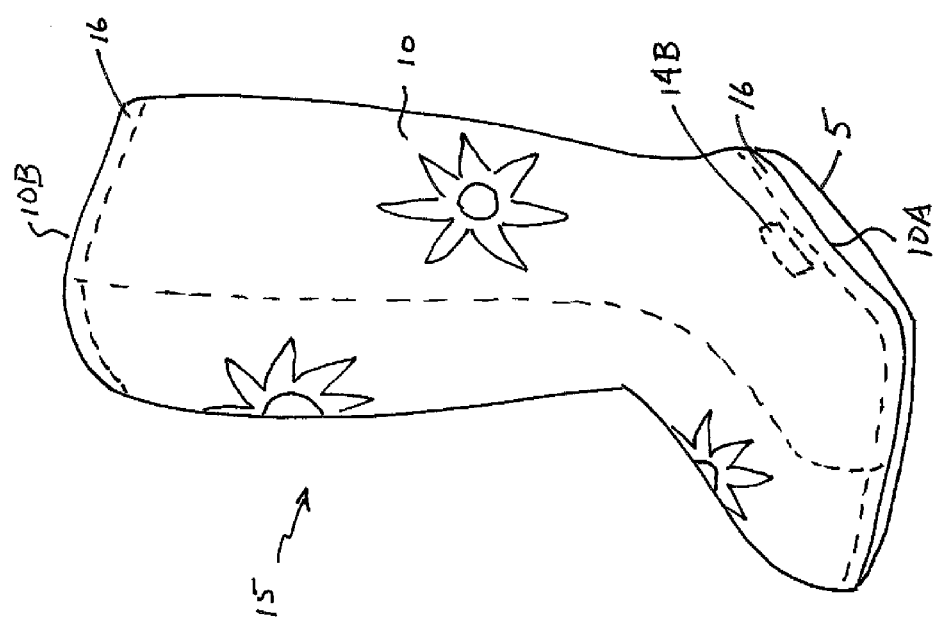
FIGS. 1A-1D illustrate perspective, front, rear, and side views of the disclosed article in relation to an orthopedic walking boot.
Figure 2B:
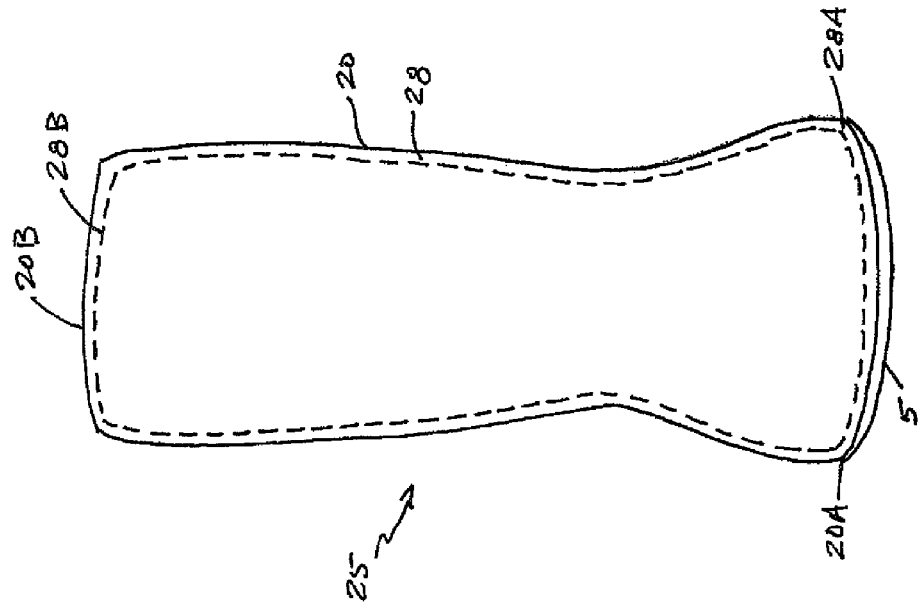
Figure 1B:
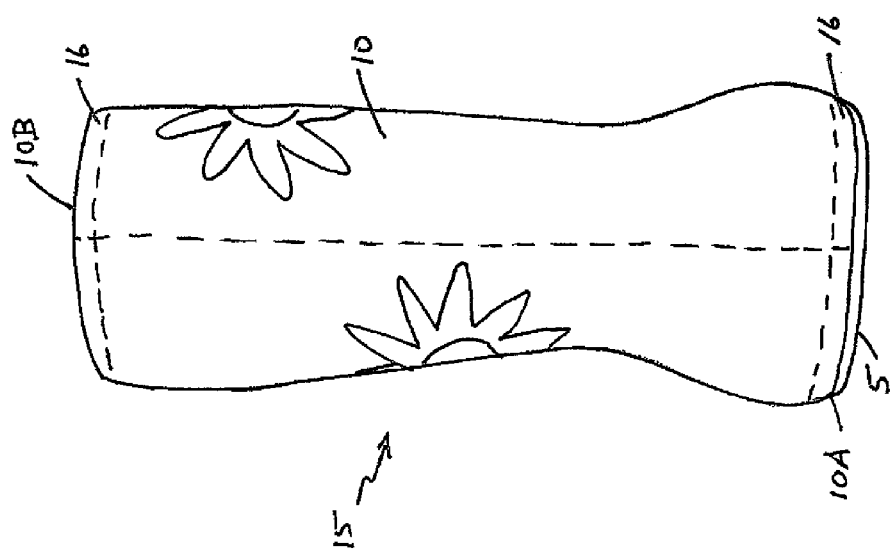
Figure 2C:
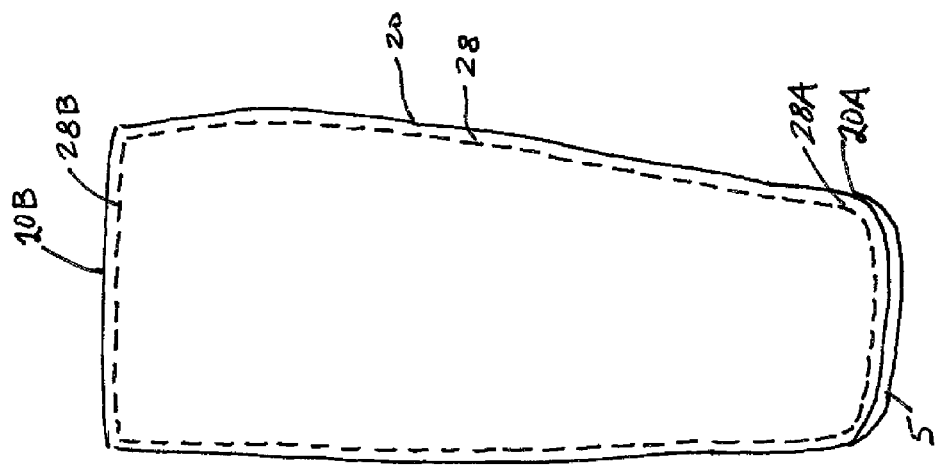
Figure 1C:
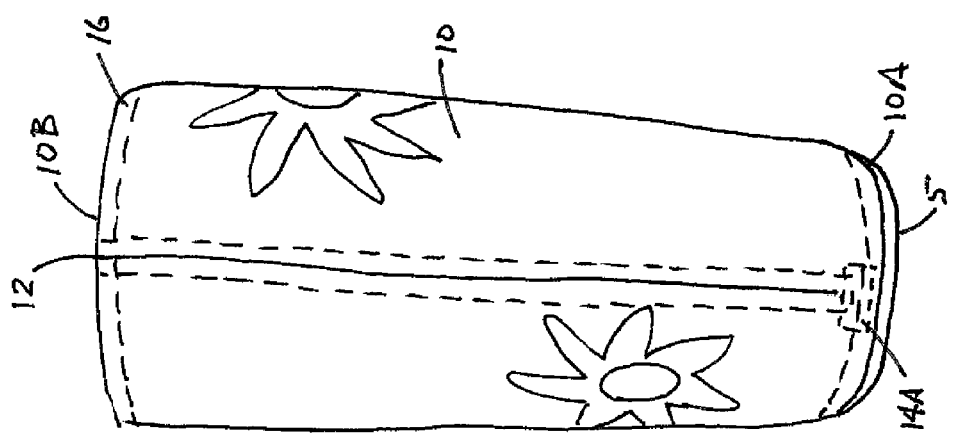
Figure 1D:
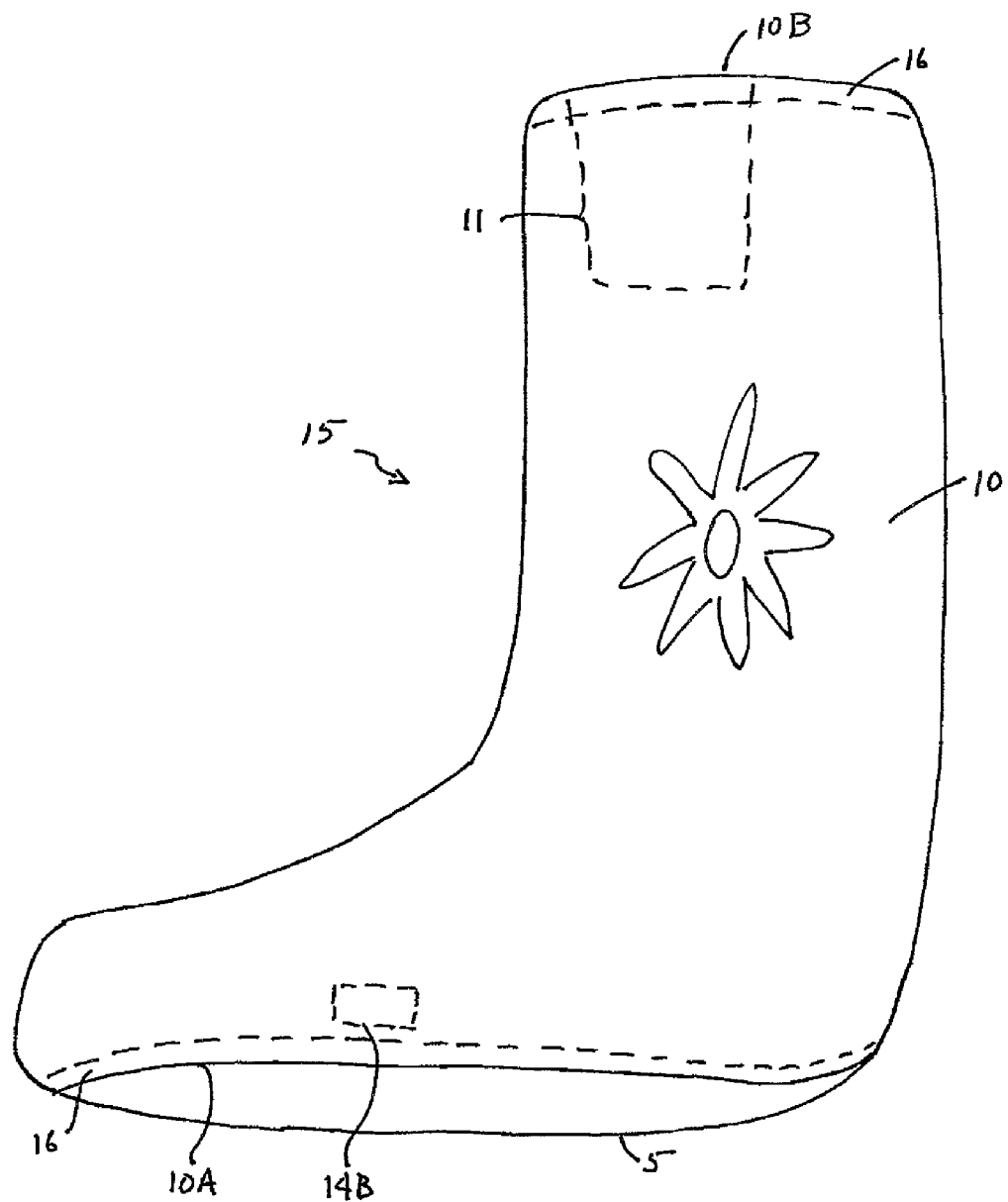

Article 15 further comprises along the backside thereof a closure mechanism 12 which may be implemented with a zipper, or equivalent mechanisms such as snaps, hooks, or a hook and pile attachment mechanism such as VELCRO®. In addition to closure mechanism 12, article 15 may further comprise one or more attachment mechanisms 14A-B, which may also be implemented with VELCRO®, and may be located at the rear and sides of the larger open end of sleeve 10 proximate end 10A. In the contemplated embodiment, either the hook or pile portion of attachment mechanisms 14A-C may be secured to sleeve 10 by sewing or equivalent attachment techniques, with the complementary portion of the mechanism securable to the boot surface. As manufactured, attachment mechanisms 14A-C, may come with the hook portion sewn to sleeve 10 while the loop or pile section is removably secured thereto with an accessible cover which may be peeled off to expose adhesive for rapid securing to the boot surface. In FIGS. 1A and 1D, the locations of attachment mechanism 14B is illustrated by its respective stitching to the inside surface of sleeve 10. Similarly, in FIG. 1C, the location of attachment mechanism 14A is illustrated by its respective stitching to the inside surface of sleeve 10 at the rear of article 15.

FIGS. 2A-2D illustrate perspective, front, rear, and side views, respectively, of a reversible article 25 in relation to orthopedic walking boot 5. Reversible article 25 is similar in design and function to article 15 in that article 25 also comprises a substantially tubular sleeve 20 having a substantially L-shaped profile with a first end 20A having an opening larger than a second end 20B thereof. Sleeve 20 is also symmetric in design and can be used on either the right or left foot. As with sleeve 10 of article 15, sleeve 20 may be formed from two pieces of material having substantially similar shapes which are sewn together along their profile images, except those edges forming either of open ends 20A and 28B. One or both ends 20A and 20B may have an elastic band 26 secured about their respective openings to ensure a close fit of sleeve 20 about the walking boot 5 and to prevent sleeve 20 from moving relative to the surface of the walking boot.

Reversible article 25 further comprises a second sleeve 28 having ends 28A and 28B similar to ends 20A and 20B of sleeve 20, respectively. Sleeve 28 maybe substantially similar in size and construction to sleeve 20. One or both of sleeves 20 and 28 may comprise material similar to sleeve 10 of article 15. Sleeves 20 and 28 are concentrically arranged and are attached at a plurality of locations, typically proximate their respective ends 20A-B and 28A-B. Sleeve 28 is illustrated conceptually in phantom in FIGS. 2A-2C relative to sleeve 20. In the illustrative embodiment, at least one surface of each of sleeves 20 and 28 is printed with graphic indicia which may comprise any of a color, pattern, logo, text, or advertisement, etc., or any combination thereof. In one illustrative embodiment, the printed graphic indicia of sleeves 20 and 28 are different in appearance. In such embodiment, because sleeve 28 and sleeve 20 are concentrically arranged and joined to form a composite sleeve, the graphic indicia printed on sleeve 20 is positioned on an exterior surface of the composite sleeve in a first configuration and the graphic indicia printed on sleeve 28 is positioned on an exterior surface of the composite sleeve in a second configuration. In this manner, given the evertable nature of article 25, the wearer may choose which of the graphic indicia is to be displayed or exposed as the covering for the orthopedic immobilization device. In an alternative embodiment, sleeve 20 and 28 may comprise materials having different characteristics, for example one sleeve comprising a water repellent material and the other sleeve comprising a less water repellent material.

Although not shown in the embodiment illustrated in the figures, reversible article 25, may include a zipper or closure mechanism extending along the back there. Article 25 further comprises one or more hook and pile attachment mechanisms 24A-B, which may also be implemented with VELCRO®, and may be located at the rear and sides of the larger open ends of each of sleeves 20 and 28. In the contemplated embodiment, either the hook or pile portion of the attachment set may be secured to sleeves 20 and 28, with the complementary portion securable to the boot surface. As manufactured, attachment mechanisms 24A-C, may come with the hook portions sewn to each of sleeves 20 and 28 with a loop or pile portion removably secured thereto and having a cover which may be peeled off to expose the adhesive for rapid securing to the boot surface.

Figure 2D:
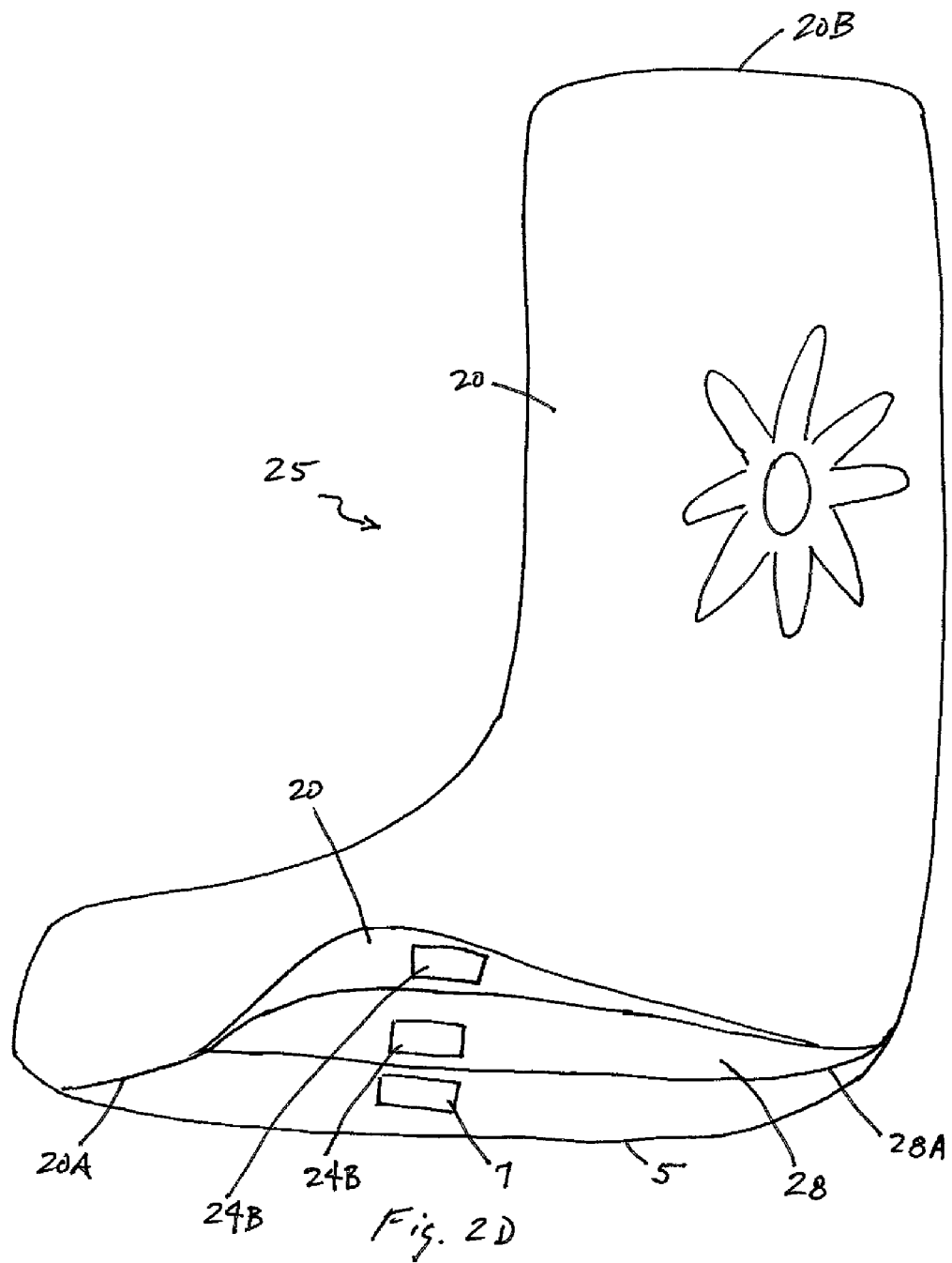
Figure 4B:
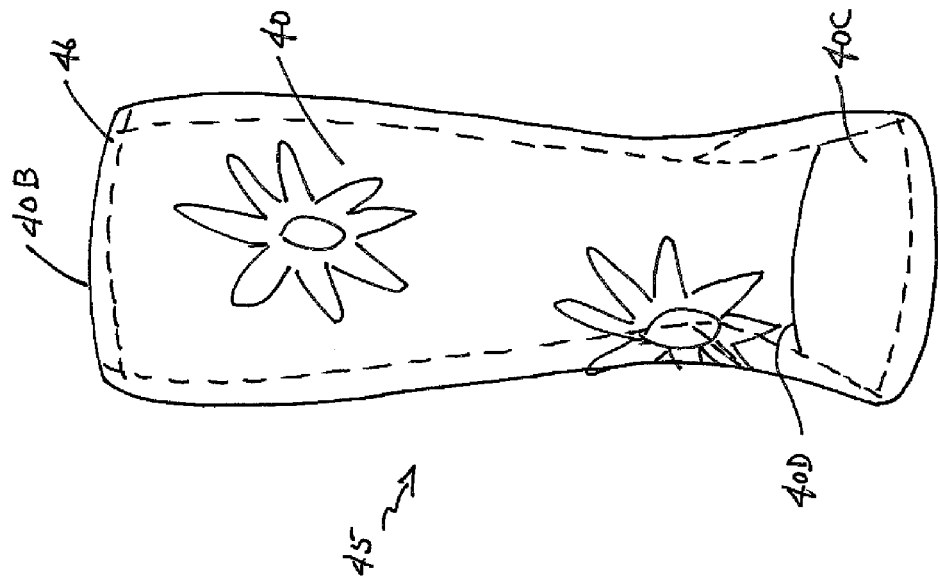
Figure 3B:
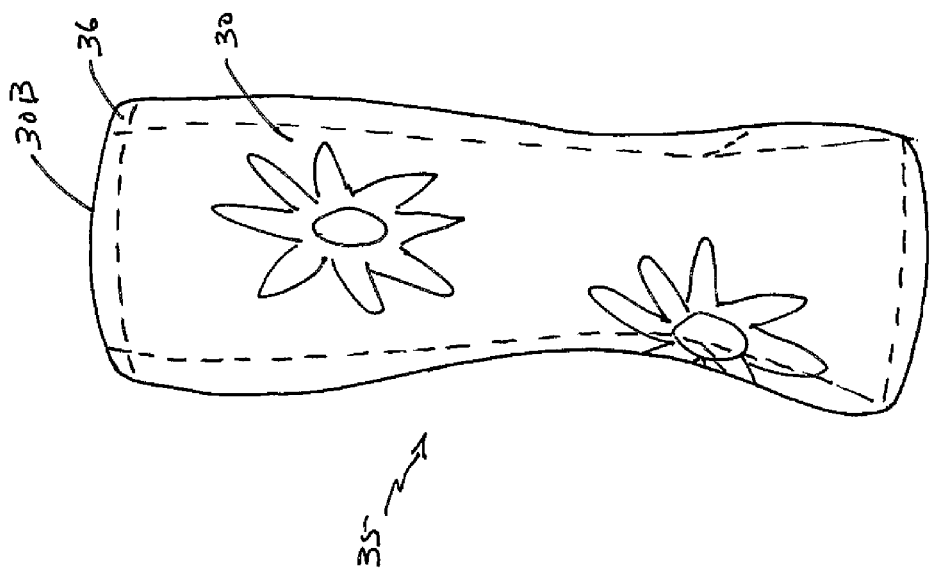
Figure 4C:
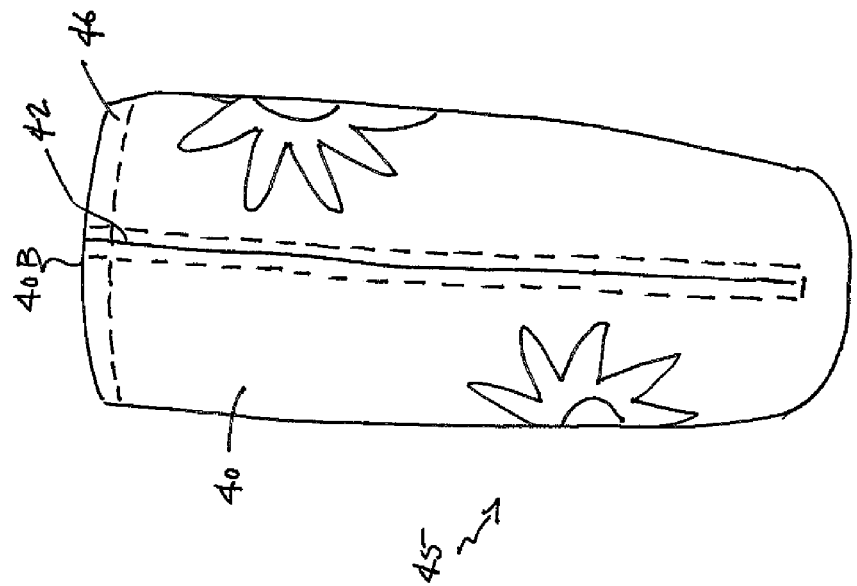
Figure 3C:
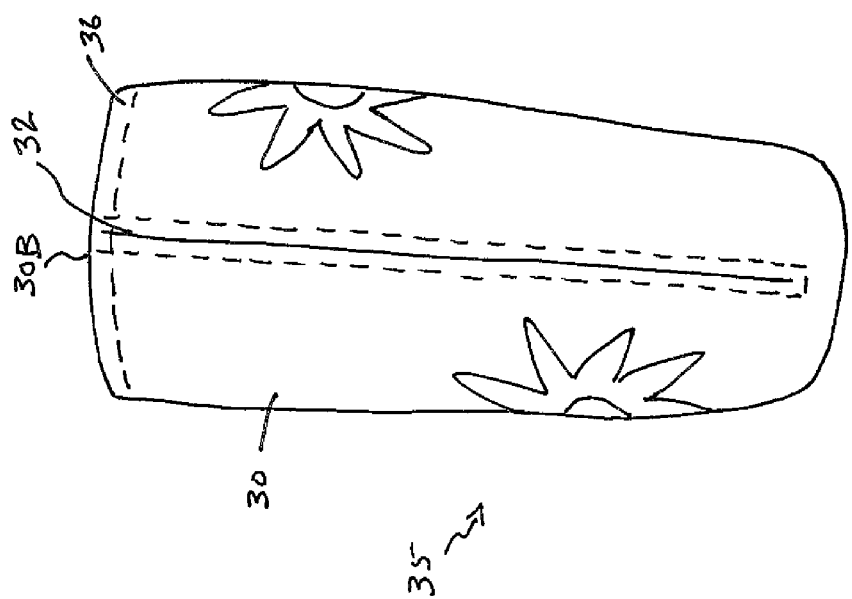
Figure 3D:
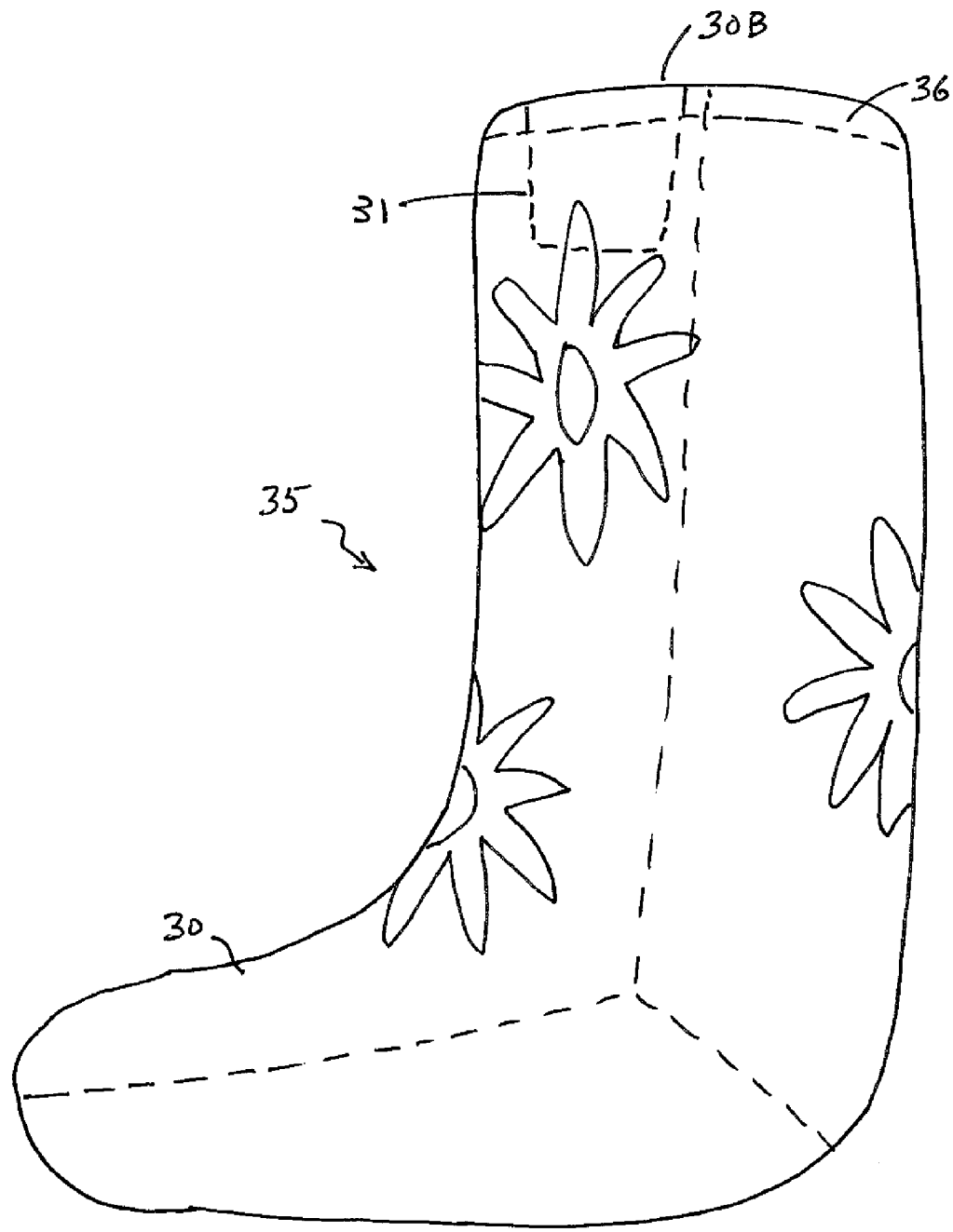
Figure 4D:
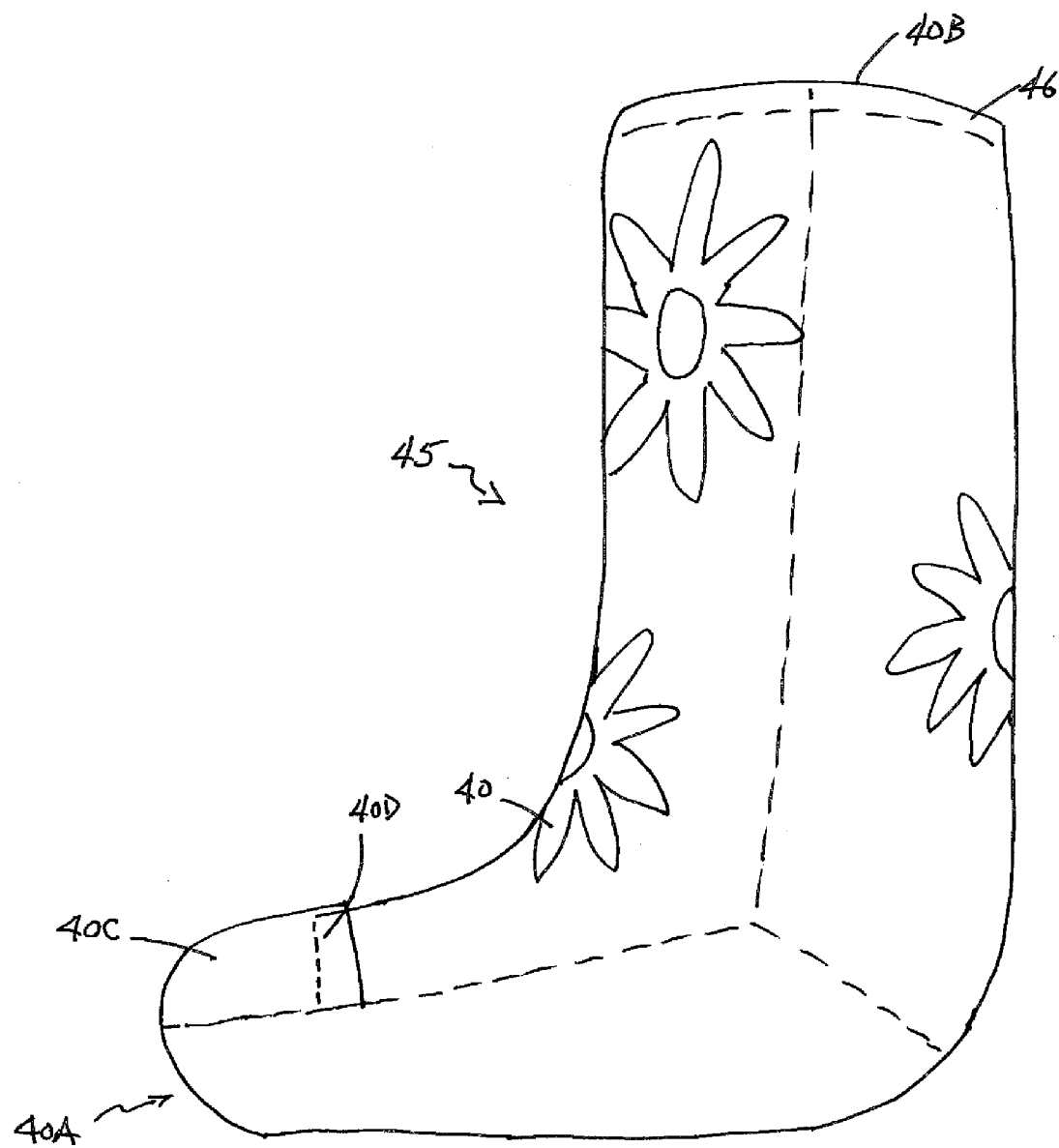

Since reversible article 25 may be everted to expose the graphic indicia on either sleeve 20 or 28, each of sleeves 20 and 28 have attachment mechanisms 24A-B secured thereto on either side of open ends 20A and 28A, respectively, as well as at the rear of the article. To facilitate attachment of the composite sleeve to a boot surface, open ends 20A and 28A are not attached to each other in the area proximate the attachment mechanisms 24A-B of either sleeve. As manufactured, attachment mechanisms 24A-B, which may be implemented with the hook portion of a hook and pile device, such as VELCRO®, are sewn to the open ends 20A and 28A of sleeves 20 and 28, respectively, while the pile portion 7 is securable to the boot surface by the wearer. In this manner, the potential for the hook portion to snag floor coverings, clothing or other materials is reduced since it is not present on the surface of the boot. As illustrated in FIG. 2D, sleeve 28 which is disposed adjacent the surface of boot 5 may be repositioned away from the sole of boot 5 to allow the hook section of attachment mechanism 24B on the inner surface of sleeve 20 to be secured to the pile section 7 of walking boot 5. In this configuration, the graphic indicia of the exterior surface of sleeve 20 is currently exposed on the exterior of article 25. A similar process may be utilized so that attachment mechanism 24B of sleeve 28 is attachable to pile 7 of boot 5 to expose the exterior surface of sleeve 28 when sleeve 20 is disposed adjacent the surface of boot 5.

FIGS. 3A-3D illustrate perspective, front, rear, and side views, respectively, of an article 35 in relation to a foot cast. Article 35 comprises a substantially tubular sleeve 30 having a substantially boot-shaped profile with a symmetric design that can be used to cover a leg cast or a below the knee cast of either the right or left foot. Article 35 surrounds the bottom of the cast and is typically used with non-weight bearing orthopedic devices. Sleeve 30 comprises an open end 30A having an elastic band 36 secured proximate thereto to facilitate a close fit of sleeve 30 about the cast or leg and to prevent sleeve 30 from moving relative to the surface thereof. Sleeve 30 may comprise material similar to sleeve 10 of article 15 and may be formed from multiple pieces of material which are sewn together, or, alternatively, from a single piece of material stitch into the sleeve configuration, as illustrated in FIG. 3E. The exemplary seams shown in FIGS. 3A-E, as well as the other figures herein, are for illustrative purposes only and are not meant to be limiting. Article 35 may further comprise an optional closure mechanism 32, such as a zipper, similar to closure mechanism 12 of article 15, for ease of application and to help maintain the article 35 in place during use.

Article 35 further comprises a pocket 31 secured to the inside surface of sleeve 30. and which may be formed of cotton, muslin, or other breathable fabric. In one embodiment, the pocket 31 may be closable using any currently known mechanism as would be understood by those skilled in the art including, but not limited to, VELCRO®, snaps, buttons, clips, etc. Pocket 31 may be used to house a scent source 70 and allows for the release of a scent to mask the inevitable pungent odor of the cast, which is one of the most common complaints of patients. Scent source 70 may have the implementation described herein. The presence of pocket 31 or scent source 70 does not interfere with the function of the cast or orthopedic device. Alternatively, pocket 31 may be sized or shaped to accommodate another object including, but not limited to those mentioned elsewhere herein. Further, the location target 31 relative to sleeve 30 may also be chosen as a matter of design choice to accommodate not only the size and shape of the object intended to be stored therein, but also the frequency of access thereto and whether the pocket is open or is closable with a closure mechanism.

An alternative embodiment of article 35 may comprise a sleeve 30 made of water repellent fabric which completely covers the cast, foot and toe. FIG. 3E illustrates an alternate embodiments to FIG. 3A in which the sleeve 30 includes a single seam extending down the front portion thereof, as illustrated.

FIGS. 4A-4D illustrate perspective, front, rear, and side views, respectively, of an article 45 in relation to a foot cast. Article 45 comprises a sleeve 40 having an opening 40A at one end thereof, and an optional closure mechanism 42 which may implemented with a zipper. Article 45 may be similar in design and function to article 35, except that article 45 further comprises an end 40A and a flap 40C which may be selectively positioned to enable the user to have their toes covered or exposed, depending on their preference and/or external temperatures. Openable end 40A has an aperture defined by a seam 40D (illustrated in Phantom in FIG. 4D) on the main portion of sleeve 40 and an edge of the flap 40C. Seam 40D may have an elastic band 46 secured along a top portion of seam. Flap 40C may be may be sized and shaped to lie over seam 40D for an enclosed toe configuration, or, flap 40C maybe retracted to under the cast, thereby allowing the toes to be exposed through the open end 40A. FIG. 4E illustrates an alternate embodiments to FIG. 4A in which the front of sleeve 40 includes a single seam extending down the front portion thereof, as illustrated. In an alternate embodiment to those illustrated in FIGS. 4D-E, the edges of flap 40C and 40D defining the aperture may include an attachment mechanism such as those described herein, including VELCRO®, to prevent the aperture from opening, for example, during inclement weather.

Figure 5A:
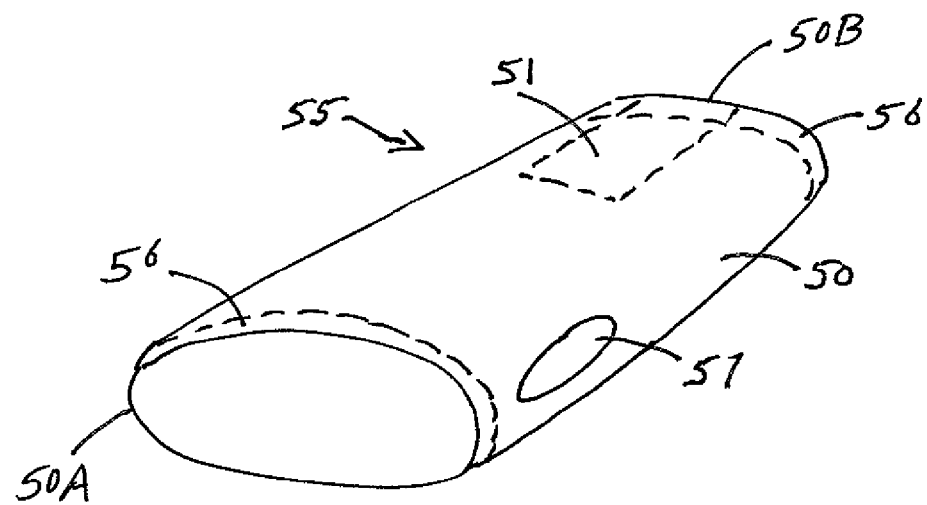
FIGS. 5A-5B illustrate side and perspective views of an embodiment of an article in relation to an arm cast.
Figure 5B:
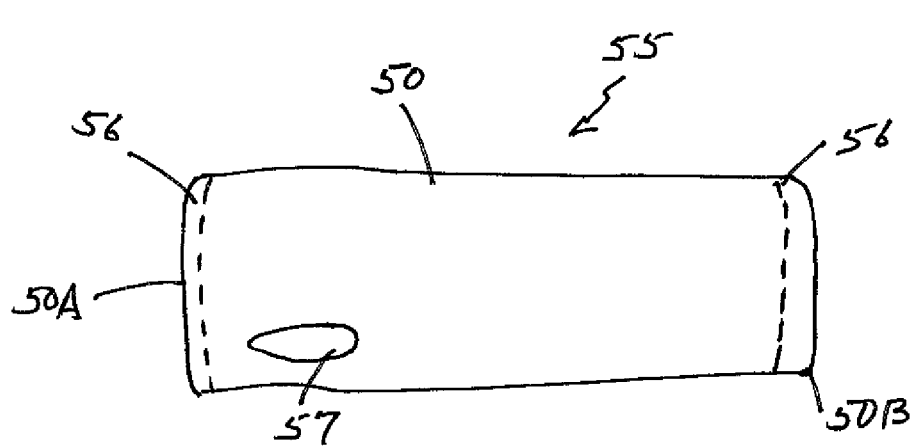

FIGS. 5A-5B illustrate perspective and side views of an article 55 for use with an arm cast. Article 55 comprises a substantially tubular sleeve 50 that can be used to cover an arm cast or a below the elbow cast of either the right or left arm. Sleeve 50 comprises an open ends 50A and 50B each having an elastic band 56 secured proximate thereto to facilitate a close fit of sleeve 50 about the cast or appendage and to prevent sleeve 50 from moving relative to the surface thereof. Sleeve 50 may comprise material similar to sleeve 10 of article 15 and may be formed from single or multiple piece(s) of material which are sewn together. Article 55 further comprises an aperture 57 located proximate one end thereof which may be designed to accommodate insertion of the wearer's thumb. In one embodiment, aperture 57 may be outlined with a different color thread or other graphic indicia different from that of the remainder of sleeve 50 to readily identify the location of aperture 57.

Article 55 further comprises a pocket 51 sewn to the inside surface of sleeve 50 and which may be formed of cotton, muslin, or other breathable fabric. Pocket 51 may be used to house a scent source 70 and allows for the release of a scent to mask the inevitable pungent odor of the cast, which is one of the most common complaints of patients. Scent source 70 may have the implementation described herein. The presence of pouch 51 or scent source 70 does not interfere with the function of the cast or orthopedic device.

An alternative embodiment of article 55, may comprise a sleeve 50 made of water repellent fabric which completely covers the cast, forearm and hand except for the fingers from. Optionally, such alternative embodiment of article 55 may further include a closure mechanism 52, such as a zipper, similar to closure mechanism 12 of article 15, for ease of application and to help maintain the article 55 in place during use.

Figure 6A:
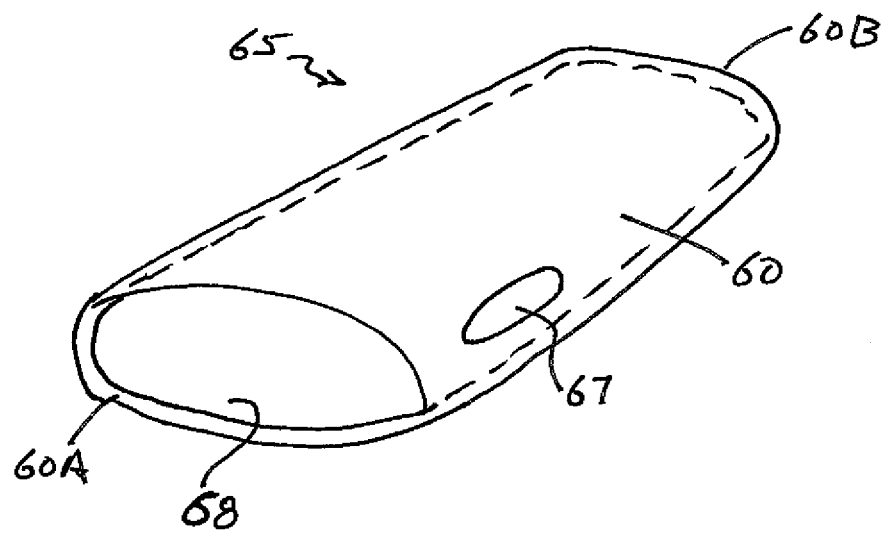
FIGS. 6A-6B illustrate side and perspective views of a reversible embodiment of the article of FIGS. 5A-5B, respectively.
Figure 6B:
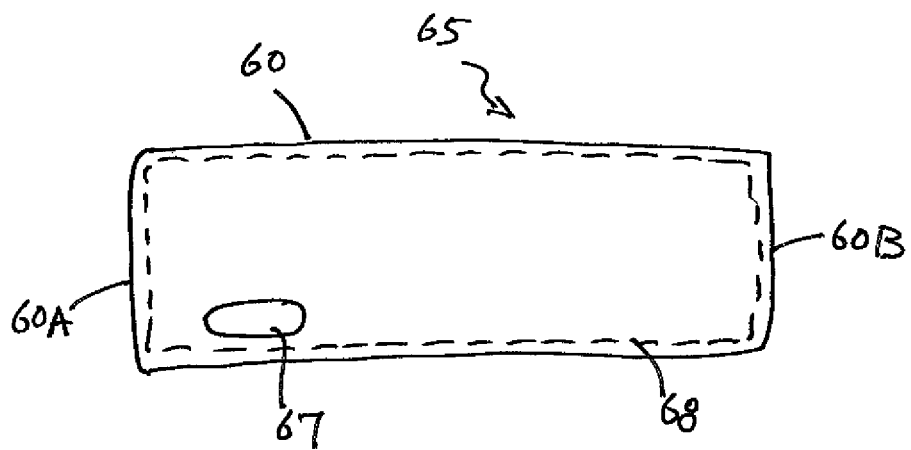

FIGS. 6A-6B illustrate perspective and side views of a reversible article 65 with an arm cast. Reversible article 65 is similar in design and function to article 55 in that article 65 also comprises a substantially tubular sleeve 60 having a first end 60A and a second end 60B. Sleeve 60 may be used on either the right or left arm. As with sleeve 50 of article 55, sleeve 60 may be formed from one or more pieces of material. One or both ends 60A and 60B may have an elastic band 66 secured about their respective openings to ensure a close fit of sleeve 60 about the cast or appendage and to prevent sleeve 60 from moving relative to the surface thereof.

Reversible article 65 further comprises a second sleeve 68 having ends 68A and 68B similar to ends 60A and 60B of sleeve 60. Sleeve 68 maybe substantially similar in size and construction to sleeve 60. One or both of sleeves 60 and 68 may comprise material similar to sleeve 10 of article 15. Sleeves 60 and 68 are concentrically arranged and may be attached at a plurality of locations, typically proximate ends 60A and 60B. Sleeve 68 is illustrated conceptually in phantom in FIG. 6 and relative to sleeve 60. In the illustrative embodiment, at least one surface of each of sleeves 60 and 68 is printed with graphic indicia which may comprise any of a color, pattern, logo, text, etc., or any combination thereof. In the illustrative embodiment, the printed graphic indicia of sleeves 60 and 68 are different in appearance. In this embodiment, because second sleeve 68 and first sleeve 60 are concentrically arranged and joined to form a composite sleeve, the graphic indicia printed on the first sleeve 60 is positioned on an exterior surface of the composite sleeve in a first configuration and the graphic indicia printed on the second sleeve 68 is positioned on an exterior surface of the composite sleeve in a second configuration. In this manner, the wearer may choose which of the graphic indicia is to be displayed or exposed as the covering for the orthopedic immobilization device. In an alternative embodiment, sleeve 60 and 68 may comprise materials having different characteristics, for example one sleeve comprising a water repellent material and the other sleeve having different characteristics.

Article 65 further comprises a pocket 61 similar to pocket 51 of article 50 which accommodates scent source 70. Pocket 61 may disposed in the space intermediate the sleeves 60 and 68 near one end thereof and may be sewn or attached to at least one of the sleeves in a manner that allows access to the pocket interior. In one embodiment, the pocket 61 may be closable using any currently known mechanism as would be understood by those skilled in the art, including, but not limited to, VELCRO®, snaps, buttons, clips, etc. Pocket 61 may be further sized and shaped to accommodate other objects such as a personal music playing device, cell phone, billfold, identification badge, credit card, etc. or other objects whose presence will not interfere with the purpose of the cast or other orthopedic device. Article 65 further comprises an aperture 67 located proximate one end thereof which may be designed to accommodate insertion of the wearer's thumb, and similar to aperture 57 of article 55.

Figure 7:
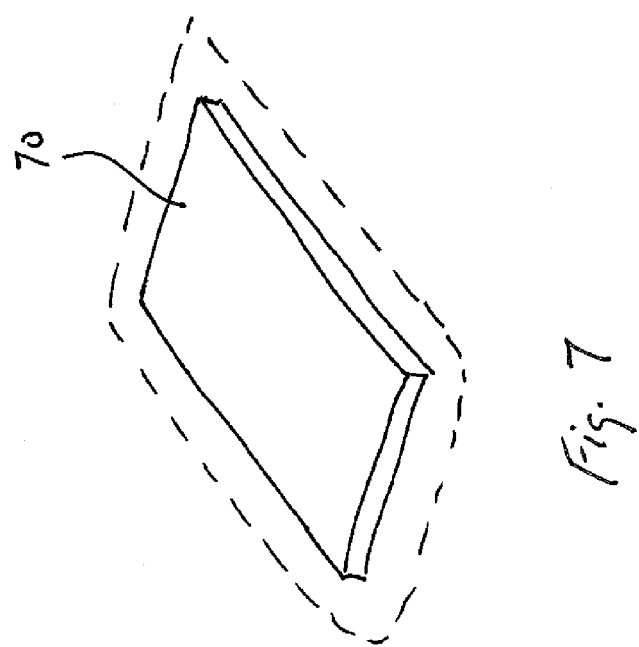
FIG. 7 is a perspective view of an implementation of the scent source which may be used with the articles disclosed herein.

FIG. 7 illustrates a scent source 70 which may be used with any of articles 15, 25, 35, 45, 55, or 65 having a pocket, illustrated conceptually in phantom, to accommodate the same. In one embodiment, the scent source 70 may comprise a carrier medium such as an absorbent, semi-flexible piece of material, including any of fabric, paper or natural or synthetic resins 02 which either a solid or liquid scent, such as a scent oil, has been impregnated in a manner which allows for gradual release of the scent therefrom. In other embodiments scent source may comprise a pouch, sachet or satchel of beads, crystals or other materials, including waxes or gels, from which the scent may emanate. In yet another, embodiment, the source 70 may include a small ampule of scented liquid which may be selectively released.

Note that although some of the embodiments disclosed in the figures described articles made of water repellent fabric, it is contemplated herein that entire article itself may be made of materials and with tolerances that effectively make it waterproof.

The present invention is illustratively described above in reference to the disclosed embodiments. Various modifications and changes may be made to the disclosed embodiments by persons skilled in the art without departing from the scope of the present invention as defined in the appended claims.

What is claimed is:

1. An article for at least partially covering an orthopedic device used for immobilization of the foot, the immobilization device having a sole portion thereof, the article comprising:
    a first sleeve of material defining exterior surface and interior surfaces and extending between first and second ends thereof, the first sleeve being substantially boot-shaped with the first sleeve end defining an opening through which a sole of the immobilization device is exposed exterior of the first sleeve when the immobilization device is disposed within the article;
    an attachment mechanism secured to the first sleeve for securing the first sleeve end adjacent the sole of the immobilization device:
    a second sleeve of material defining exterior surface and interior surfaces extending between first and second ends thereof; and
    a second elastic member secured about one of the first and second ends of the second sleeve.

2. The article of claim 1 further comprising graphic indicia printed on one of the exterior surface and interior surfaces of the first sleeve.

3. The article of claim 2 wherein:
the second sleeve and first sleeve are concentrically arranged and joined to form a composite sleeve, and
wherein the graphic indicia printed on the first sleeve is positioned on an exterior surface of the composite sleeve in a first configuration and graphic indicia printed on the second sleeve is positioned on an exterior surface of the composite sleeve in a second configuration.

4. The article of claim 1 further comprising:
a plurality of attachment mechanisms secured to the interior surface of the first sleeve proximate one of the first and second ends of the first sleeve.

5. The article of claim 4 wherein the plurality of attachment mechanisms comprise one of a hook and pile attachment set.

6. The article of claim 1 further comprising a pocket attached to the first sleeve.

7. The article of claim 6 in combination with a scent source retainable within the pocket.

8. The article of claim 1 further comprising an aperture proximate a toe portion thereof for providing selective access to an interior portion of the sleeve.

9. The article of claim 1 wherein both the first and second sleeves have a substantially L-shaped profile with one of the first and second sleeve ends, respectively, defining an opening larger than the other of the first and second sleeve ends.

10. The article of claim 1 further comprising:
a plurality of attachment mechanisms secured to the interior surface of the first and second sleeves proximate one of the first and second sleeve ends thereof, respectively.

11. The article of claim 10 wherein the a plurality of attachment mechanisms comprise one of a hook and pile attachment set.

12. The article of claim 1 wherein the first sleeve comprises a fabric having elastic properties.

13. An article for covering an orthopedic immobilization device, the article comprising:
first and second sleeves of material, each sleeve defining exterior and interior surfaces thereof and extending between first and second ends thereof;
first elastic members secured about one of the first and second ends of each of the first and second sleeves;
graphic indicia printed on one of the exterior surface and interior surfaces of each of the first and second sleeves;
the first and second sleeves being concentrically arranged and joined to form a composite sleeve having evertable interior and exterior surfaces,
wherein the graphic indicia printed on the first sleeve is positioned on an exterior surface of the composite sleeve in a first configuration and the graphic indicia printed on the second sleeve is positioned on an exterior surface of the composite sleeve in a second configuration.

14. The article of claim 13 further comprising:
second elastic members secured about other of the first and second ends of each of the first and second sleeves.

15. The article of claim 13 further comprising:
an aperture extending through the first and second sleeves proximate one of first and second ends thereof and sized to allow a digit to extend therethrough when the article is disposed about an appendage.

16. The article of claim 13 wherein the first and second sleeves each have a substantially L-shaped profile with one sleeve end defining an opening larger than an other sleeve end.

17. The article of claim 16 further comprising:
at least one attachment mechanism secured to the interior surface of each of the first and second sleeves proximate the sleeve end defining a larger opening so that the attachment mechanism is securable to an orthopedic device in each of the first and second composite sleeve configurations.

18. The article of claim 17 wherein the attachment mechanism comprises one of a hook and pile attachment set with the other of the hook and pile attachment set securable to an orthopedic device.

19. The article of claim 13 further comprising:
an aperture extending through the composite sleeve proximate an end thereof and sized to allow a digit to extend there through when the article is disposed about the immobilization device.

20. The article of claim 13 further comprising:
a pocket attached to the interior surface of one of the first and second.

21. An article for covering an orthopedic immobilization device, the article comprising:
a sleeve of material defining exterior surface and interior surfaces and having a substantially boot-shaped profile and a first open end and a second end, the second end of the sleeve proximate a toe portion of the boot-shaped profile;
an aperture proximate the second end and extending partially across the width of the sleeve and defining first and second adjacent portions of the sleeve adjacent the aperture; and
wherein one of the first and second adjacent portions of the sleeve adjacent the aperture is shaped to overlap the aperture and the other portion adjacent the aperture to selectively enable one of access to an interior portion of the sleeve through the aperture and covering of the aperture.

22. The article of claim 21 further comprising a pocket attached to the interior surface of the first sleeve.

23. The article of claim 22 in combination with a scent source retainable within the pocket.

24. The article of claim 21 further comprising:
an elastic member secured about one of the first and second adjacent portions of the sleeve adjacent the aperture.

25. The article of claim 21 wherein the sleeve is made of a substantially stretchable material and wherein one of the portions of the sleeve adjacent the aperture is a stretchable to selectively expose an interior portion of the sleeve.

26. The article of claim 21 further comprising:
a closure mechanism secured to the sleeve for enabling selective access to an interior portion of the sleeve.

* * * * *

UNITED STATES PATENT AND TRADEMARK OFFICE
CERTIFICATE OF CORRECTION

PATENT NO. : 8,430,829 B1
APPLICATION NO. : 12/725996
DATED : April 30, 2013
INVENTOR(S) : Kelly Marchetti It is certified that error appears in the above-identified patent and that said Letters Patent is hereby corrected as shown below:

In the Claims:

In Column 8, line 59 (Claim 1), "device:" should read -- device; --

In Column 9, line 30 (Claim 11), "the a plurality" should read -- the plurality --

Signed and Sealed this
Eleventh Day of June, 2013

Teresa Stanek Rea
*Acting Director of the United States Patent and Trademark Office*